(12) United States Patent
Redlingshoefer et al.

(10) Patent No.: US 8,609,576 B2
(45) Date of Patent: *Dec. 17, 2013

(54) CATALYSTS CONTAINING TUNGSTATE FOR THE SYNTHESIS OF ALKYL MERCAPTAN AND METHOD FOR THE PRODUCTION THEREOF

(75) Inventors: Hubert Redlingshoefer, Muenchsteinach (DE); Christoph Weckbecker, Grundau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/546,585

(22) Filed: Jul. 11, 2012

(65) Prior Publication Data

US 2012/0277095 A1 Nov. 1, 2012

Related U.S. Application Data

(62) Division of application No. 12/796,079, filed on Jun. 8, 2010, now Pat. No. 8,372,780, which is a division of application No. 11/570,102, filed as application No. PCT/EP2005/000721 on Jul. 5, 2005, now Pat. No. 7,759,523.

(30) Foreign Application Priority Data

Aug. 4, 2004 (DE) .......................... 10 2004 037 739

(51) Int. Cl.
*B01J 23/00* (2006.01)
*C01G 41/02* (2006.01)

(52) U.S. Cl.
USPC ...................... 502/317; 502/304; 423/594.13

(58) Field of Classification Search
USPC ......... 502/317, 304; 423/263, 594.13; 568/71
See application file for complete search history.

(56) References Cited

U.S. PATENT DOCUMENTS

| 2,828,052 A | 1/1958 | Folkins et al. |
| 4,442,308 A | 4/1984 | Arntz et al. |
| 5,852,219 A | 12/1998 | Sauer et al. |
| 7,989,731 B2 | 8/2011 | Bischoff et al. |
| 2006/0229474 A1 | 10/2006 | Barth et al. |

FOREIGN PATENT DOCUMENTS

| EP | 0 068 193 A1 | 1/1983 | |
| EP | 0 832 667 A2 | 4/1998 | |
| EP | 0 832 878 A2 | 4/1998 | |
| EP | 2005021491 A1 | 3/2005 | |
| WO | WO 03-091360 | * 11/2003 | ............... C10G 9/18 |

OTHER PUBLICATIONS

S. Stevenson and P.A. Sermon. Promotion of Nitrogen and Hydrogen Chemisorption and Ammonia Synthesis on Alumina-supported Hexagonal Tungsten Bronze, Kx WO, J. Chem. Soc., Faraday Trans. I , 1987,83, 2175-2191 (Faraday Symposium 21).*
B. Ingham, S. C. Hendy, S. V. Chong, and J. L. Tallon. Density-functional studies of tungsten trioxide, tungsten bronzes, and related systems, Phys. Rev. B, 72, 075109, 2005.*
Mashkina, A. V. et al., "Activity of tungstete Catalysts in the Synthesis of Metylmercaptane from Methanol and Hydrogen Sulfide," Reaction Kinetics and Catalysis Letters, Mar. 1983, pp. 159-164, vol. 36, No. 1, Akedémiai Kiadó, co-published with Springer Science+Business Media B.V., Formerly Kiuwar Academic Publishers B.V., Amsterdam. The Netherlands.
Gerhartz, Wolfgang at as,. "Aluminum Oxide," Ullmann 's Encyclopedia of Industnel Chemistry, 1985, pp. 381-062, 5$^{th}$ completely revised edition, VCH Verlagsgesellschaft mbH, Weinheim, Federal Republic of Germany.
Laruelle at al, High-Energy Milling of WO3 Oxides: Amorphization and Reaction with CsCO3. Journal of Solid State Chemistry III, 172:177, 1994.
A. Ovenston J.R, Walls. S. Mirl, T. Ramdeen. The DC and AC electrical characteristics of composite mixed conductor catalysts at high temperatures, J. Phys D: Appl. Phys. 1988, 21, 17i3-1781.
T.I. Drobasheva, T.S. Skoropad, G.A. Bukhalova. Potassium tungstate-tungsten(VI) oxide system, Zhurnal Neorganicheskoi Khimii 1977, 22(7), abstract.

* cited by examiner

*Primary Examiner* — Carlos Barcena
(74) *Attorney, Agent, or Firm* — Smith, Gambrell & Russell, LLP

(57) ABSTRACT

The invention relates to a catalyst containing alkali tungstate for the synthesis of alkylmercaptanes from alkanols and hydrogen sulphide, in addition to a method for the production of said catalyst, wherein the molar ratio of alkali to tungstan is <2:1.

6 Claims, No Drawings

CATALYSTS CONTAINING TUNGSTATE FOR THE SYNTHESIS OF ALKYL MERCAPTAN AND METHOD FOR THE PRODUCTION THEREOF

CROSS-REFERENCE TO RELATED APPLICATIONS

This application is a divisional of U.S. Ser. No. 12/796,079 filed Jun. 8, 2010, which is a divisional of U.S. Ser. No. 11/570,102 filed Dec. 6, 2006, which is the National Stage of International Application No. PCT/EP2005/007211 filed Jul. 5, 2005, which claims, the benefit of priority of German Application No. 10 2004 037 739.1 filed Aug. 4, 2004, each of which are incorporated herein by reference.

BACKGROUND OF THE INVENTION

The present invention relates to a catalyst comprising alkali metal tungstate for the synthesis of alkyl mercaptans from alkanols and hydrogen sulphide, and to a process for preparing this catalyst.

In this patent application, the term alkali is understood to mean the bound alkali metals of the Periodic Table of the Elements or mixtures of at least two alkali metals bound in the tungstates. In this case, cesium occurs only together with a further element of the alkali metal group.

Methyl mercaptan in particular is an industrially important intermediate, for example for the synthesis of methionine and for the synthesis of dimethyl sulphoxide and dimethyl sulphone. It is nowadays prepared predominantly from methanol and hydrogen sulphide by reaction over a catalyst composed of aluminium oxide. The methyl mercaptan is synthesized commonly in the gas phase at temperatures between 300 and 500° C. and at pressures between 1 and 25 bar.

In addition to the methyl mercaptan formed, the reaction mixture comprises the unconverted starting materials and by-products, for example dimethyl sulphide and dimethyl ether, and also the gases which are inert for the purposes of the reaction, for example methane, carbon monoxide, hydrogen and nitrogen. The methyl mercaptan formed is removed from this reaction mixture.

For the economic viability of the process, a maximum selectivity is required in the catalytic reaction of methanol and hydrogen sulphide to give methyl mercaptan in order to keep the removal of the methyl mercaptan formed from the reaction mixture as uncomplicated and inexpensive as possible. Here, especially the energy demands for the cooling of the reaction gas mixture to condense the methyl mercaptan constitute a large cost factor.

To increase activity and selectivity, aluminium oxide as a support is typically admixed with potassium tungstate or cesium tungstate. In this case, the tungstate is commonly used in amounts up to 25% by weight based on the total weight of the catalyst. An improvement of activity and selectivity is also obtained by increasing the molar ratio of hydrogen sulphide to methanol. Typically, molar ratios between 1 and 10 are employed.

However, a high molar ratio also means a high excess of hydrogen sulphide in the reaction mixture and thus the need to conduct large amounts of gas in circulation. To reduce the energy demands required for this purpose, the ratio of hydrogen sulphide to methanol should therefore deviate only slightly from 1.

U.S. Pat. No. 2,820,062 relates to a process for preparing organic thiols, in which a catalyst composed of active aluminium oxide which is admixed with potassium tungstate in an amount of 1.5 to 15% by weight, based on the weight of the catalyst, is used. With this catalyst, good activities and selectivities are achieved at reaction temperatures of 400° C. and molar ratios of 2. This US patent mentions various possibilities for the introduction of the potassium tungstate into the aluminium oxide. For instance, it is said to be possible to employ impregnation processes, coprecipitations and pure mixtures. Little significance is attributed to the actual preparation of the catalyst for the economic viability of the synthesis process of methyl mercaptan.

EP 0 832 687 B1 describes the advantages of the use of cesium tungstate ($Cs_2WO_4$) instead of potassium tungstate ($K_2WO_4$) as a promoter. For instance, use of cesium tungstate can achieve an enhanced activity with simultaneously good selectivity.

Increasing the cesium tungstate concentration to up to 40% by weight allows the selectivity for methyl mercaptan to be increased to 92% without the activity being disproportionately worsened.

According to the general view, the best selectivity is achieved with catalysts for which the alkali metal/tungsten ratio is equal to 2:1 (A. V. Mashkina et al., React. Kinet. Catal. Lett., Vol. 36, No. 1, 159-164 (1988).

SUMMARY OF THE INVENTION

It is an object of the present invention to specify a catalyst and a process for its preparation, which, at low molar ratios of hydrogen sulphide to methanol, features improved activity and selectivity compared to the known catalysts and thus leads to better economic viability of the process.

This object is achieved by the provision of a catalyst comprising a catalytically active alkali metal tungstate which contains bound alkali metals and tungsten with a molar ratio of alkali metals to tungsten of <2:1, in particular of <2:1 to 0.9:1, preferably 1.9:1 to 1:1, particularly 1.6:1 to 1:1.

The oxidic composition can be described with the formula $A_xWO_y$ in which A is alkali metal and x' is <2 to 0.9 and y is 3.4 to <4.

The bound alkali metal constituent of the tungstate can be composed of one or more elements of the alkali metal group. In this case, cesium occurs only in combination with another alkali metal element.

The catalyst contains the tungstate in an amount of 8 to 45% by weight, in particular 15 to 36% by weight, preferably >25 to 36% by weight. In the case of a coated catalyst, these proportions are based on the composition of the coating.

The oxidic compounds composed of alkali metal(s) and tungsten may be impregnated directly onto a support body (supported catalyst).

In the case of the preparation of catalysts in the form of extrudates or mouldings, the pulverulent support is impregnated or mixed with the oxidic composition and the resulting intermediate is subsequently reshaped (unsupported catalyst). When a coated catalyst is prepared, the pulverulent support is impregnated with the catalytically active composition and the resulting mixture is then applied to a preferably inert support core in the form of a coating.

The alkali metal/W ratio preferably ranges from <1.9:1 to 1:1. The inventive catalysts for the reaction of alkanols with hydrogen sulphide to give alkyl mercaptans thus comprise a superstoichiometric proportion of tungsten compared to the catalyst impregnated with cesium tungstate ($Cs_2WO_4$) or potassium tungstate ($K_2WO_4$) according to the prior art.

It is found that this higher proportion in the tungstate on the aluminium oxide used with preference in comparison to the stoichiometric alkali metal tungstate used exclusively in the prior art imparts to the catalyst an improved activity with simultaneously improved selectivity. While the increase in the concentration of cesium tungstate ($Cs_2WO_4$) on the catalyst merely brings about an increase in the selectivity with simultaneously lower activity, a further increase in the selectivity with simultaneously increased activity is unexpectedly found in the case of the increase in the tungsten content in relation to the alkali metal content. According to the invention, an excellent activity can be achieved at very high loadings with the promoter without the activity of the catalyst, as known from the prior art, decreasing. In addition, it has also been found that the activity and selectivity of the catalyst can be adjusted precisely via the alkali metal-tungsten ratio and via the selection of the alkali metals. When mixtures of alkali metals are used, it is additionally possible to replace the comparatively more expensive metals such as cesium or rubidium at least partly with less expensive metals, for example potassium or sodium, without the activity or selectivity of the catalyst being impaired.

DETAILED DESCRIPTION OF THE INVENTION

The catalyst is used in the form of a supported catalyst in which the surface is impregnated with the catalytically active substance, or of a coated catalyst in which a preferably inert core is surrounded with a mixture of catalytically active substance and support material. In addition, extrudates or mouldings in which the catalytically active substance is mixed with the pulverulent support material before the reshaping or is impregnated with it may be used. The support materials used are the known oxidic inorganic compounds, for example $SiO_2$, $TiO_2$, $ZrO_2$ and preferably what is known as active aluminium oxide. This material has high specific surface areas between about 10 and 400 $m^2/g$, and consists mainly of oxides of the transition series of the crystallographic phases of aluminium oxide (see, for example, Ullmann's Encyclopaedia of Industrial Chemistry of 1985, Vol. A1, pages 561-562). These transition oxides include $\gamma$-, $\delta$-, $\eta$-, $\kappa$-, $\chi$- and $\theta$-aluminium oxide. All of these crystallographic phase are converted on heating of the aluminium oxide to temperatures above 1100° C. to the thermally stable $\alpha$-aluminium oxide. Active aluminium oxide is supplied commercially for catalytic applications in various qualities and supply forms. Particularly suitable for the preparation of supported catalysts are support bodies composed of granulated or extruded aluminium oxide having particle diameters of 1 to 5 mm, a specific surface area of 180 to 400 $m^2/g$, a total pore volume between 0.3 and 1.2 ml/g, and a bulk density of 300 to 900 g/l. For the purposes of the invention, preference is given to using aluminium oxide having a specific surface area of more than 200 $m^2/g$, since the catalytic activity of the finished catalyst rises slightly with increasing surface area of the aluminium oxide. This material is used in powder form preferably for the preferred of the coated catalysts, extrudates or mouldings.

The aqueous impregnation solution for the application of the promoter can be prepared in a simple manner from water-soluble alkali metal and tungsten compounds, in particular tungstic acid ($H_2WO_4$) and alkali metal hydroxides. To this end, for example, tungstic acid is suspended in water and dissolved with addition of a base and heating. Alkali metal hydroxide or another alkali metal salt is likewise dissolved in water and combined with the solution of tungstic acid (promoter solution). Also advantageously usable are alkali metal salts whose anions can be driven out without residue by heat treatment, for example nitrates, formates, oxalates, acetates or carbonates. Suitable for stabilizing this solution having a pH of 8 to 14 are inorganic and also organic bases. Preference is given to using those bases which can be driven out without residue by a final heat treatment of the catalyst obtained after the impregnation. These bases preferably include ammonium hydroxide and organic bases, in particular amines. Compared to the prior art, the molar ratio of alkali metals and W when the aqueous impregnation solution is prepared is selected in such a way that, in contrasts to cesium tungstate ($Cs_2WO_4$) or potassium tungstate ($K_2WO_4$) having an alkali metal/W ratio of 2 to 1, a higher proportion of tungsten, i.e. an alkali metal to W ratio of less than 2 to 1, in particular <1.9:1 to 0.9:1, is present. In comparison to the known catalysts, this leads to a distinctly increased activity and selectivity of the inventive catalysts, in particular at low ratios of hydrogen sulphide and methanol in the reaction gas.

When mixtures of tungstates with mixed alkali metal fractions are used, they are preferably two different alkali metals of the Periodic Table in a ratio between 0.01:1.0 and 1.0:1.0. In this case, the proportion of the less expensive alkali metal is preferably increased to such an extent and simultaneously that of the comparatively more expensive alkali metal reduced in return that no deterioration in the activity or selectivity of the catalyst occurs.

For the application of the promoter solution, various impregnation techniques, such as immersion impregnation, spray impregnation, vacuum impregnation and pore volume impregnation may be used, and the impregnation may also be effected repeatedly. In the case of mouldings, the selected impregnation process has to enable the desired loading amount of the promoter to be applied with good uniformity over the total cross section.

The promoter solution is preferably applied to the shaped bodies by spray or vacuum impregnation in one or two steps. In spray impregnation, the aqueous impregnation solution is sprayed onto the support bodies. In vacuum impregnation, a reduced pressure is generated by means of a vacuum pump in a vessel charged with the shaped bodies. Opening of a hose connection to the aqueous impregnation solution sucks the solution into the vessel until the entire bed of shaped bodies is covered with the solution. After an impregnation time of 0.2 to 2 hours, the solution which has not been absorbed by the material is drained off or poured off.

Predrying at room temperature for a period of 1 to 10 hours allows the initial concentration gradient over the cross section of the shaped bodies to be substantially balanced. Thus, the uniformity of the impregnation over the cross section of the catalyst particles is improved. Preference is given to drying the thus obtained catalyst precursors to remove the residual moisture at 100 to 200° C., preferably 100 to 140° C., for the period of 1 to 10 hours. There is then a calcination at 300 to 600° C., preferably 420 to 480° C., for the period of 1 to 20 hours, preferably 1 to 5 hours. This fixes the promoter on the aluminium oxide and decomposes and drives off the base of the impregnation solution. Optionally, the bed of support bodies of the catalyst precursors can be flowed through by a gas stream in the course of the predrying, drying and calcinations, which improves the removal of the residual moisture and of the decomposition gases.

The shaped bodies can also be impregnated in a plurality of stages, in particular two stages.

In a preferred embodiment, the solution used in the first stage then comprises one to two thirds of the intended total amount of alkali metal and tungsten compounds.

When the procedure has a plurality of stages, but at least two stages, the precursor obtained in the first step is optionally not calcined.

Otherwise, the same impregnation, drying and calcination programme as described for the one-stage process proceeds in the second stage.

This multistage impregnation is viable in particular when high loadings are desired and/or the limited solubility of the promoter mixture does not enable the loading in one step.

The possibility also exists of spraying the support bodies repeatedly with the impregnation solution during the impregnation operation (step a) and, between these treatment steps, in each case removing portions of the residual moisture at a temperature of up to 120° C., before moving on to step b.

In the preparation of the coated catalyst, the powder to be applied as a coating may be calcined before or after the coating. For example, this catalyst type may be prepared according to EP-B-0 068 193. In the preparation of the extrudates or of the mouldings too, the calcinations may be effected before and/or after the reshaping.

EXAMPLES

Example 1

Comparative Example 150 g of aluminium oxide I were impregnated with 21.0% by weight of cesium tungstate ($Cs_{2.0}WO_4$) with the aid of vacuum impregnation. To this end, the specific procedure was as follows:

To prepare the impregnation solution, 55.7 g of tungstic acid were suspended in 44.5 g of water and dissolved by adding 111.4 g of 25% ammonia solution and heating to 50° C. 74.6 g of $Cs(OH) \cdot H_2O$ were dissolved in 37.3 g of water and mixed with the first solution. The solution was subsequently stirred in a covered beaker for 48 hours. Thereafter, the solution was made up to a volume of 234 ml with 25 g of water.

The aluminium oxide was initially charged in a glass vessel which was evacuated to 150 mbar. By virtue of the opening of a tap, the impregnation solution was sucked into the evacuated glass vessel until the entire bed of shaped bodies was covered with the solution. After a wait time of 15 minutes and aeration of the glass vessel, the solution which had not been absorbed by the aluminium oxide ran back into the beaker. 79 ml of impregnation solution were absorbed by the aluminium oxide.

The granules were dried to remove the residual moisture at room temperature in an air current for the period of 1 hour and subsequently at 120° C. for 3 hours. Afterward, the granules were calcined at 455° C. for 3 hours.

Example 2

Comparative Example

Comparative Example 1 was repeated with 26.3% loading of the aluminium oxide with cesium tungstate ($Cs_{2.0}WO_4$).

Example 3

Comparative Example

Comparative Example 1 was repeated with 19.6% loading of the aluminium oxide with potassium tungstate ($K_{2.0}WO_4$) with use of KOH instead of $CS(OH) \cdot H_2O$.

Example 4

150 g of aluminium oxide (Spheralite 501A) was impregnated in a two-stage impregnation with a total of 26.7% by weight of promoter ($K_{1.6}WO_y$) with the aid of vacuum impregnation. The specific procedure was as follows:

64.5 g of tungstic acid were suspended in 50.7 g of water and dissolved by adding 126.9 g of 25% ammonia solution and heating to 50° C. 22.9 g of KOH were dissolved in 11.5 g of water and mixed with the first solution. The solution was subsequently stirred in a covered beaker for 48 hours. Thereafter, the solution, was made up to a volume of 234 ml with 39 g of water. The aluminium oxide was, initially charged in a glass vessel which was evacuated to 150 mbar. By virtue of the opening of a tap, the impregnation was sucked in until the entire bed of mouldings was covered with the solution. After a wait time of 15 minutes and aeration of the glass vessel, the solution which had not been absorbed by the aluminium oxide flowed back into the beaker. 76 ml of impregnation solution were absorbed by the aluminium oxide. Subsequently; the granules were dried at room temperature for 1 hour and at 120° C. for 3 hours, and calcined at 455° C. for 3 hours.

To carry out the second impregnation, an identical impregnation solution to that in the first step was prepared and applied in the same way by vacuum impregnation to the already laden catalyst from the first step. This was then followed again by drying at room temperature for 1 hour, followed by drying at 120° C. for 3 hours. Finally; the catalyst particles were calcined under air at 455° C. for 4 hours.

Example 5

150 g of aluminium oxide (Spheralite 501A) was impregnated in a two-stage impregnation with a total of 30.1% by weight of promoter ($Rb_{0.9}WO_y$) with the aid of vacuum impregnation. The specific procedure was as follows:

59.0 g of tungstic acid were suspended in 48.3 g of water and dissolved by adding 110.7 g of 25% ammonia solution and heating to 50° C. 41.5 g of RbOH were dissolved in 17.5 g of water and mixed with the first solution. The solution was subsequently stirred in a covered beaker for 48 hours. Thereafter, the solution was made up to a volume of 234 ml with 25 g of water. The aluminium oxide was initially charged in a glass vessel which was evacuated to 150 mbar. By virtue of the opening of a tap, the impregnation was sucked in until the entire bed of mouldings was covered with the solution. After a wait time of 15 minutes and aeration of the glass vessel, the solution which had not been absorbed by the aluminium oxide flowed back into the beaker. 75 ml of impregnation solution were absorbed by the aluminium oxide. Subsequently, the granules were dried at room temperature for 1 hour and at 120° C. for 3 hours, and calcined at 455° C. for 3 hours.

To carry out the second impregnation, an identical impregnation solution to that in the first step was prepared and applied in the same way by vacuum impregnation to the already laden catalyst from the first step. This was then followed again by drying at room temperature for 1 hour, followed by drying at 120° C. for 3 hours. Finally, the catalyst particles were calcined under air at 455° C. for 4 hours.

Example 6

150 g of aluminium oxide (Spheralite 501A) was impregnated in a two-stage impregnation with a total of 29.4% by weight of promoter ($K_{0.7}Cs_{0.7}WO_y$) with the aid of vacuum impregnation. The specific procedure was as follows:

61.3 g of tungstic acid were suspended in 49.1 g of water and dissolved by adding 122.7 g of 25% ammonia solution and heating to 50° C. 9.8 g of KOH and 29.0 g of $Cs(OH) \cdot H_2O$ were dissolved in 14.5 g of water and mixed with the first solution. The solution was subsequently stirred in a covered beaker for 48 hours. Thereafter, the solution was made up to a volume of 234 ml with 47 g of water. The aluminium oxide was initially charged in a glass vessel which was evacuated to 150 mbar. By virtue of the opening of a tap, the impregnation was sucked in until the entire bed of mouldings was covered with the solution. After a wait time of 15 minutes and aeration of the glass vessel, the solution which had not been absorbed by the aluminium oxide flowed back into the beaker. 75 ml of impregnation solution were absorbed by the aluminium oxide. Subsequently, the granules were dried at room temperature for 1 hour and at 120° C. for 3 hours, and calcined at 455° C. for 3 hours.

To carry out the second impregnation, an identical impregnation solution to that in the first step was prepared and applied in the same way by vacuum impregnation to the already laden catalyst from the first step. This was then followed again by drying at room temperature for 1 hour, followed by drying at 120° C. for 3 hours. Finally, the catalyst particles were calcined under air at 455° C. for 4 hours.

Example 7

150 g of aluminium oxide (Spheralite 501A) was impregnated in a two-stage impregnation with a total of 31.0% by weight of promoter ($Na_{0.3}Cs_{1.1}WO_y$) with the aid of vacuum impregnation. The specific procedure was as follows:

61.1 g of tungstic acid were suspended in 48.9 g of water and dissolved by adding 122.1 g of 25% ammonia solution and heating to 50° C. 3.2 g of NaOH and 44.6 g of Cs(OH)·$H_2O$ were dissolved in 22.3 g of water and mixed with the first solution. The solution was subsequently stirred in a covered beaker for 48 hours. Thereafter, the solution was made up to a volume of 234 ml with 40 g of water. The aluminium oxide was initially charged in a glass vessel which was evacuated to 150 mbar. By virtue of the opening of a tap, the impregnation was sucked in until the entire bed of mouldings was covered with the solution. After a wait time of 15 minutes and aeration of the glass vessel, the solution which had not been absorbed by the aluminium oxide flowed back into the beaker. 74 ml of impregnation solution were absorbed by the aluminium oxide. Subsequently, the granules were dried at room temperature for 1 hour and at 120° C. for 3 hours, and calcined at 455° C. for 3 hours.

To carry out the second impregnation, an identical impregnation solution to that in the first step was prepared and applied in the same way by vacuum impregnation to the already laden catalyst from the first step. This was then followed again by drying at room temperature for 1 hour, followed by drying at 120° C. for 3 hours. Finally, the catalyst particles were calcined under air at 455° C. for 4 hours.

Example 8

Use Example

The catalysts were tested with regard to their performance data in the synthesis of methyl mercaptan from hydrogen sulphide and methanol.

The synthesis was carried out in a stainless steel tube of internal diameter 18 mm and a length of 500 mm. The catalyst bed of in each case 76 ml was secured in the reaction tube on both sides by inert beds of glass spheres. The reaction tube was heated to the reaction temperature of about 320° C. using a jacket comprising a thermal oil.

The experimental conditions can be taken from the following list:
GHSV: 1300 $h^{-1}$ (based on standard conditions)
LHSV: 0.84 $h^{-1}$ (based on liquid MeOH)
Reaction temperature: 320° C.
Mass ratio
$H_2S$/MeOH: 1.9
Pressure: 9 bar The reaction mixture comprising the products methyl mercaptan, dimethyl sulphide and dimethyl ether, and comprising the unconverted starting materials methanol and hydrogen sulphide is analyzed by online gas chromatography.

When the tungsten fraction in relation to the alkali metal fraction in the catalyst is increased, a distinct increase in activity can be seen with simultaneously improved selectivity. In comparison to the prior art, this leads to a yield increase of up to 10%. The selectivity can be increased to up to ~96.5% by adjusting the metal-tungstate ratio, and the methanol conversion rises. In the industrial scale synthesis of methyl mercaptan, this also leads to considerable cost savings in the removal of the reaction products from unconverted methanol and by-products.

In addition, the results of Examples 4 to 7 show that at least a portion of the alkali metals can be exchange for one another in order to selectively adjust the activity and selectivity of the catalyst or in order to save raw material costs in the catalyst synthesis.

TABLE 1

Experimental results

| Catalyst Example | Alkali metal | mol. alkali metal:W ratio | Loading [% by wt.] | Methanol conversion [%] | Selectivity [%] | Yield [%] |
|---|---|---|---|---|---|---|
| CE1 | Cs | 2:1 | 21.0 | 82.4 | 93.3 | 76.9 |
| CE2 | Cs | 2:1 | 26.3 | 79.5 | 94.7 | 75.2 |
| CE3 | K | 2:1 | 19.6 | 76.0 | 95.2 | 72.4 |
| E4*) | K | 1.6:1 | 26.7 | 85.6 | 95.1 | 81.4 |
| E5*) | Rb | 0.9:1 | 30.1 | 73.2 | 96.6 | 70.7 |
| E6*) | K, Cs | 1.4:1 | 29.4 | 88.5 | 95.4 | 84.4 |
| E7*) | Na, Cs | 1.4:1 | 31.0 | 88.4 | 95.8 | 84.7 |

CE1: Catalyst according to Comparative Example 1
*)multistage impregnation

The invention claimed is:

1. A supported catalyst comprising a catalytically active tungstate which contains chemically bound potassium with a potassium to tungsten molar ratio of <2:1 to 0.9:1.

2. The catalyst according to claim 1, wherein the potassium to tungsten molar ratio is 1.9:1 to 1:1.

3. The catalyst according to claim 2, wherein the potassium to tungsten molar ratio is 1.6:1 to 1:1.

4. A supported catalyst comprising a catalytically active tungstate which contains chemically bound potassium with a potassium to tungsten molar ratio of <2:1 to 0.9:1, wherein the tungstate is present is in an amount of 8 to 45% by weight.

5. The catalyst according to claim 4, comprising the tungstate in an amount of 15 to 36% by weight.

6. The catalyst according to claim 5, comprising the tungstate in an amount >25 to 36% by weight.

* * * * *